US006184438B1

(12) United States Patent
Hannah

(10) Patent No.: US 6,184,438 B1
(45) Date of Patent: Feb. 6, 2001

(54) MUTANT GENES ENCODING PLANT ADP-GLUCOSE PYROPHOSPHORYLASE AND METHODS OF USE

(75) Inventor: L. Curtis Hannah, Gainesville, FL (US)

(73) Assignee: University of Florida, Gainesville, FL (US)

(*) Notice: Under 35 U.S.C. 154(b), the term of this patent shall be extended for 0 days.

(21) Appl. No.: 09/195,966

(22) Filed: Nov. 19, 1998

(51) Int. Cl.[7] ............................ C12N 15/29; C12N 15/54; C12N 5/04; C12N 15/82; A01H 5/00

(52) U.S. Cl. ................... 800/284; 800/320.1; 435/101; 435/194; 435/419; 435/468; 536/23.6

(58) Field of Search ...................... 536/23.6; 435/419, 435/101; 800/284, 320.1, 194, 468

(56) References Cited

U.S. PATENT DOCUMENTS

| | | | |
|---|---|---|---|
| 5,589,618 | 12/1996 | Hannah et al. | 800/205 |
| 5,650,557 | 7/1997 | Hannah et al. | 800/205 |

FOREIGN PATENT DOCUMENTS

| | | |
|---|---|---|
| 9309237 | 5/1993 | (WO) . |
| 9810082 | 3/1998 | (WO) . |
| 9822601 | 5/1998 | (WO) . |

OTHER PUBLICATIONS

Anderson, J. et al. (1989) "The Encoded Primary Sequence of a Rice Seed ADP–glucose Pyrophosphorylase Subunit and Its Homology to the Bacterial Enzyme" The Journal of Biological Chemistry 264(21):12238–12242.

Anderson, J. et al. (1991) "Molecular characterization of the gene encoding a rice endosperm–specific ADP glucose pyrophosphorylase subunit and its developmental pattern of transcription" Gene. 97:199–205.

Bae, J. et al. (1990) "Cloning and Characterization of the Brittle–2 Gene of Maize[1,2]" Maydica 35:317–322.

Bhave, M. et al. (1990) "Identification and Molecular Characterization of Shrunken–2 cDNA Clones of Maize" The Plant Cell 2:581–588.

Copeland, L. et al. (1981) "Purification of Spinach Leaf ADPglucose Pyrophosphorylase[1]" Plant Physiol. 68:996–1001.

Dickinson, D. et al. (1969) "Presence of ADP–Glucose Pyrophosphorylase in Shrunken–2 and Brittle–2 Mutants of Maize Endosperm[1]" Plant Physiol. 44:1058–1062.

Hannah, L. et al. (1975) "Characterization of Adenosine Diphosphate Glucose Pyrophosphorylases from Developing Maize Seeds[1,2,3]" Plant Physiol. 55:297–302.

Hannah, L. et al. (1976) "Characterization of ADP–Glucose Pyrophosphorylase from Shruken–2 and Brittle–2 Mutants of Maize[1]" Biochemical Genetics 14(7,8):547–560.

Morell, M. et al. (1988) "Affinity Labeling of the Allosteric Activator Site(s) of Spinach Leaf ADP–glucose Pyrophosphorylase" The Journal of Biological Chemistry 263(2):633–637.

Muller–Rober, B. et al. (1990) "One of two different ADP–glucose pyrophosphorylase genes from potato responds strongly to elevated levels of sucrose" Mol. Gen. Genet. 224:136–146.

Nakata, P. et al. (1991) "Comparison of the primary sequences of two potato tuber ADP–glucose pyrophosphorylase subunits" Plant Molecular Biology 17:1089–1093.

Okita, T. et al. (1990) "The Subunit Structure of Potato Tuber ADPglucose Pyrophosphorylase[1]" Plant Physiol. 93:785–790.

Olive, M. et al. (1989) "Isolation and nucleotide sequences of cDNA clones encoding ADP–glucose pyrophosphorylase polypeptides from wheat leaf and endosperm" Plant Molecular Biology 12:525–538.

Shaw, J. et al. (1992) "Genomic Nucleotide Sequence of a Wild–Type Shrunken–2 Allele of Zea mays[1]" Plant Physiol. 98:1214–1216.

Stark, D. et al. (1992) "Regulation of the Amount of Starch in Plant Tissues by ADP Glucose Pyrophosphorylase" Science 258:287–292.

Tsai, C. et al. (1966) "Starch–Deficient Maize Mutant Lacking Adenosine Diphosphate Glucose Pyrophosphorylase Activity" Science 151:341–343.

Giroux, M.J. et al. (1994) "ADP–glucose pyrophosphorylase in shrunken–2 and brittle–2 mutants of maize" Molecular & General Genetics 243(4):400–408.

Lal, Shailesh et al. (1999) "The AG Dinucleotide Terminating Introns Is Important but Not Always Required for Pre–mRNA Splicing in the Maize Endosperm" Plant Physiology 120(1):65–72.

Parera, Carlos A. et al. (1996) "Improving vigor in shrunken–2 corn seedlings" Journal of the American Society for Horticultural Science 121(6):1069–1075, abstract only.

Clancy, M. et al. (1994) "Maize shrunken–1 intron and exon regions increase gene expression in maize protoplasts" Plant Science 98:151–161.

Lou, H. et al. (1993) "3' Splice Site Selection in Dicot Plant Nuclei Is Position Dependent" Mol. Cell. Biol. 13(8):4485–4493.

McCullough, A.J. et al. (1993) "Factors Affecting Authentic 5' Splice Site Selection in Plant Nuclei" Mol. Cell. Biol. 13(3):1323–1331.

(List continued on next page.)

Primary Examiner—David T. Fox
(74) Attorney, Agent, or Firm—Saliwanchik, Lloyd & Saliwanchik

(57) ABSTRACT

The present invention pertains to mutant alleles of the genes encoding the large subunit of AGP-glucose pyrophosphorylase in plants. When present in maize plants, these mutant alleles confer enhanced germination characteristics but without any dimishment of food quality or flavor as compared to plants that express the sh2-R genes. The subject invention also concerns methods for transforming plants with the mutant alleles. The subject invention also concerns plants that have the mutant alleles of the invention incorporated in their genome.

7 Claims, 10 Drawing Sheets

OTHER PUBLICATIONS

Weil, C.F. et al. (1990) "The Effects Of Plant Transposable Element Insertion On Transcription Initiation And RNA Processing" Annu. Rev. Plant Physiol. Plant Mol. Biol. 41:527–552.

Barta, A. et al. (1986) "The expression of nopaline synthase–human growth hormone chimaeric gene in transformed tobacco and sunflower callus tissue" Plant Mol. Biol. 6:347–357.

Brown, J.W.S. (1996) "Arabidopsis intron mutations and pre–mRNA splicing" Plant J. 10(5):771–780.

Callis, J. et al. (1987) "Introns increase gene expression in cultered maize cells." Genes & Development 1:1183–1200.

Carle–Urioste, J.C. et al. (1994) "In vivo analysis of intron processing using splicing–dependent reporter gene assays" Plant Mol. Biol. 26:1785–1795.

Golovkin, M. et al. (1996) "Structure and Expression of a Plant U1 snRNP 70K Gene: Alternative Splicing of U1 snRNP 70K Pre–mRNAs Produces Two Different Transcripts" Plant Cell 8:1421–1435.

Goodall, G.J. et al. (1989) "The AU–Rich Sequences Present in the Introns of Plant Nuclear Pre–mRNAs Are Required for Splicing" Cell 58:473–483.

Goodall, G.J. et al. (1991) "Different effects of intron nucleotide composition and secondary structure on pre–mRNA splicing in monocot and dicot plants" EMBO J. 10(9):2635–2644.

Gorlach, J. et al. (1995) "Organ–specific differences in the ratio of alternatively spliced chorismate synthase (LeCS2) transcripts in tomato" Plant J. 8(3):451–456.

Keith, B. et al. (1986) "Monocot and dicot pre–mRNAs are processed with different efficiencies in transgenic tobacco" EMBO J. 5(10):2419–2425.

Kiss–Laszlo, Z. et al. (1995) "Splicing of cauliflower mosaic virus 35S RNA is essential for viral infectivity" EMJO J. 14(14):3552–3562.

Luehrsen, K.R. et al. (1994) "Intron creation and polyadenylation in maize are directed by AU–rich RNA" Genes & Development 8:1117–1130.

Moore, M.J. et al. (1993) "Evidence of two active sites in the spliceosome provided by stereochemistry of pre–mRNA splicing" Nature 365:364–368.

Moore, M.J. et al. (1993) "Splicing of Precursors to mRNAs by the Spliceosome" In *The RNA World*, R. Gesteland and J. Atkins, eds. (Cold Spring Harbor Laboratory Press), pp. 303–308.

Nishihama, R. et al. (1997) "Possible involvement of differential splicing in regulation of the activity of Arabidopsis ANP1 that is related to mitogen–activated protein kinase kinase kinases (MAPKKKs)" Plant J. 12(1):39–48.

Pautot, V. et al. (1989) "Expression of a mouse metalothionein gene in transgenic plant tissue" Gene 77:133–140.

Sharp P.A. (1994) "Split Genes and RNA Splicing" Cell 77:805–815.

Simpson, G.G., et al. (1996) "Mutation of putative branchpoint consensus sequences in plant introns reduces splicing efficiency" Plant J. 9(3):369–380.

Simpson, G.G., et al. (1996) "Splicing of precursors to mRNA in higher plants: mechanism, regulation and sub–nuclear organisation of the spliceosomal machinery" Plant Mol. Biol. 32:1–41.

van Santen, V.L. et al. (1987) "Splicing of plant pre–mRNAs in animal systems and vice versa" Gene 56:253–265.

Vasil, V. et al. (1989) "Increased Gene Expression by the First Intron of Maize Shrunken–1 Locus in Grass Species" Plant Physiol. 91:1575–1579.

Wang et al. Plant J. 11(5):1121–1126, 1997.*

Greene et al. Plant Physiol. 112(3):1315–1320, 1996.*

* cited by examiner

```
-1020  TGATGCTTTTCCTGGGCAGGAGGAGAGCTATGAGACGTATGTCCTCAAAGCCACTTTGCAT
 -960  TGTGTGAAACCAATATGATCTTTGTTACTTCATCATGAACATTGTGAAACTAC
 -900  TAGCTTACAAGCATTAGTGACAGCTCAGAAAAAAGTTATCTCTGAAAGGTTTCATGTGTA
 -840  CCGTGGGAAATGAGAAAGGTGTCTAAACTATGAACACCTTCAATATGTGTTTGCAGGCAAA
 -780  CTCTTCTGGAAGAAAGGTGTCTAAACTATGAACACCTTCAATATGTGTTTGCAGGCAAA
 -720  CTGTGCATTTTGGAAGTATCATCTATAGATGTCTGTTGAGGGGAAAGCCGTACGCCAACG
 -660  TTATTACTCAGAAACAGCTTCAACACAGTTGTCTGCTTTATGATGGCATCTCCACCC
 -600  AGGCACCCATCACCTATTCACCTTGTTGCAAACATGCATAGGCATATCAATATGCTCATTTA
 -540  GATCATAAAAAATCATTAAGAGTTTGCAAACATGCATAGGCATATCAATATGCTCATTTA
 -480  TTAATTTGCTAGCAGATCATCTTCCTACTCTTTACTTATTTATTGTTGAAAATATGT
 -420  CCTGCACCTAGGGAGCTCGTATACAGTAGTACCAATGCATCTTCATTAAATGTGAATTTCAGA
 -360  AAGGAAGTAGGAACCTATGAGAGTATTTTTCAAAATTAATTAGCGGCTTCTATTATGTTT
 -300  ATAGCAAAGGCCAAGGCAAAATCGGAACACTAATGATGGTTGGTTGCATGAGTCTGTCG
 -240  ATTACTTGCAAGAAATGTGAACCTTTGTTCTGCGTGGGCATAAAACAAACAGCTTCT
 -180  AGCCTCTTTTACGTGACTTGCACTTGCAAGAGAAATGTGAACTCCTTTCATTTCTGTATGT
 -120  GGACATAAATGCCAAAGCATCCAGGCTTTTCATGGTTGTTGATGTCTTTACACAGTTCAT
  -60  CTCCACCAGTATGCCCCTCCTCGGAGGCAAGTGTGATTTCGACCTTGCAGCCACCTTTTTTGTTCTG
    1  ACAAGATCACTTCGGGAGGCAAGTGTGATTTCGACCTTGCAGCCACCTTTTTTGTTCTG
   61  TTgtaagtatactttcccttaccatctttatctgtagttagtttaattgtaattgggaagta
  121  ttagtggaaagaggatgagatgctatcatctatgtactctgcaaatgcatctgacgttat
  181  atgggctgcttcatataatttgaattgctccattcttgccgacaatatattgcaaggtat
  241  atgcctagttccatcaaaagttctgtttcattctaaaagcatttagtggcacgcaa
  301  tttgtccatgagggaaaggaaatctgtttggttacttgcttgaggtgcattcttcat
  361  atgtccagtttatggaagtaataaacttcagtttggtcataagatgtcatatattaaagg
  421  caaacatatattcaatgttcaattcatcgtaaatgttccctttttgtaaaagattgcata
  481  ctcatttatttgagttgcagtGTATCTAGTAGTTGGAGGAGATATGCAGTTTGCACTTG
```

FIG. 1A

M   Q   F   A   L
541  CATTGGACACGAACTCAGGTCCTCACCAGATAAGATCTTGTGAGGGTGATGGATTGACA
      A   L   D   T   N   S   G   P   H   Q   I   R   S   C   E   G   D   G   I   D
601  GGTTGGAAAATTAAGTATTGGGGCAGAAAGCAGAGAAAGCTTTGAGAATAGGTGCT
      R   L   E   K   L   S   I   G   G   R   K   Q   E   K   A   L   R   N   R   C
661  TTGGTGGTAGAGTTGCTGCAACTACACAATGTATTCTTACCTCAGATGCTTGTCCTGAAA
      F   G   G   R   V   A   A   T   Q   C   I   L   T   S   D   A   C   P   E
721  CTCTTgtaagtatccacctcaattattactcttactgtggttggtttacttagtttgtct
      T   L
781  tttcaagggaaattactgtatttttgtgtttgtgggagttctatactctgttggac
841  tggttattgtaaagatttgttcaaataggtcatctaataattgttgaaatctgggaac
901  tgtggtttcactgcgttcaggaaaaagtgaattattggttactgcatgaataacttatgg
961  aaatagacctagagttgctgcattacatataactgcaactcctagtgcgttcaaaaaaaaa
1021 gtctctttcgacctcgcattacatataactgcaactcctagtgcgttcaaaaaaaaa
1081 atgcaactcttagaacgctcacagtgtaatctttcctgaattgtattaatggcatgt
1141 atgcactacttgtatactctaggattaagtaatctaactctaggcccatatttgca
1201 gCATTCTCAAACACAGTCCTCTAGGAAAAATTATGCTGATGCAAACCGTGTATCTGCTAT
      H   S   Q   T   Q   S   R   K   N   Y   A   D   A   N   R   V   S   A   I
1261 CATTTTGGGCGGAGGCACTGGAGTCCTCAGCTCTCTTCCCTGACAAGCACAAGAGCTACGCC
      I   L   G   G   T   G   S   Q   L   F   P   L   T   S   T   R   A   T   P
1321 TGCTgtaagggataacactgaacatccaacgttgattactctattatagtattatacaga
      A
1381 ctgtactttcgaatttatctagtttctacacatatttagtggattcttctcattttca
1441 agatacacaattgatccataatcgaagtggtatgtaagacagtggagttaaaagattatat
1501 tttttgggagacttccagtcaaatttcttagaagtttttttggtccagatgttcataaa

FIG. 1B

```
1561  gtcgccgcttcatactttttaattggtgcactattagGTACCTGTTGGA
                                           V  P  V  G
1621  GGATGTTACAGGCTTATTGATATCCCTATGAGTAACTGCTTCAACAGTGGTATAAATAAG
       G  C  Y  R  L  I  D  I  P  M  S  N  C  F  N  S  G  I  N  K
1681  ATATTTGTGATGAGTCAGTTCAATTCTACTTCGCTTAACCGCCATATTCATCGTACATAC
       I  F  V  M  S  Q  F  N  S  T  S  L  N  R  H  I  H  R  T  Y
1741  CTTGAAGGCGGATCAACTTTGCTGATGGATCTGTACAGgtgattacctcatccttgttg
       L  E  G  G  I  N  F  A  D  G  S  V  Q
1801  atgtgtaatactgtaattaggagtagatttgtgtggagagaataataaacagatgccgag
1861  attctttctaaaagtctagatccaaaggcattgtggttcaaaacactatggacttctac
1921  catttatgtcattactttgcctaatgttccattgaatgggcaaatattattgattctaca
1981  agtgtttaattaaaaactaattgttcatcctgcagGTATTAGCGGCTACACAAATGCCTG
                                           V  L  A  A  T  Q  M  P
2041  AAGAGCCAGCTGGATGGTTCCAGGGTACAGCAGACTCTATCAGAAAATTTATCTGGGTAC
       E  E  P  A  G  W  F  Q  G  T  A  D  S  I  R  K  F  I  W  V
2101  TCGAGgtagttgatatttctcgtttatgaatgtccattcactcattcctgtagcattgt
       L  E
2161  ttctttgtaatttgagtctcctgtattctttagGATTATTACAGTCACAAATCCATT
                                         D  Y  Y  S  H  K  S  I
2221  GACAACATTGTAATCTTGAGTGGCGATCAGCTTTATCGGATGAATTACATGGAACTTGTG
       D  N  I  V  I  L  S  G  D  Q  L  Y  R  M  N  Y  M  E  L  V
2281  CAGgtatggtgttctcttgttcctcatgttccgtaatgtcctgattttggattaacca
       Q
2341  actactttggcatgcattattccagAAACATGTCGAGGACGATGCTGATATCACTATA
                                 K  H  V  E  D  D  A  D  I  T  I
```

FIG. 1C

```
2401  TCATGTGCTCCTGTTGATGAGAGgtaatcagttgttatatcatcctaatatgaatatgt
       S  C  A  P  V  D  E  S
2461  catcttgttatccaacacaggatgcatatggtctaatctgcttcctttttcccttc
2521  ggaagCCGAGCTTCTAAAAATGGGCTAGTGAAGATTGATCATACTGGACGTGTACTTCAA
                R  A  S  K  N  G  L  V  K  I  D  H  T  G  R  V  L  Q
2581  TTCTTTGAAAAACCAAAGGGTGCTGATTTGAATTCTATGgttagaaattcctgtgtaat
       F  F  E  K  P  K  G  A  D  L  N  S  M
2641  ccaattcttttgtttcctctttcttgagatgaacccctcttttagttattccatgg
2701  ataacctgtacttgacttattcagaaatgattttctatttgctgtagaatctgacacta
2761  aagctaatagcactgatgtgtgcagAGAGTTGAGACCAACTTCCTGAGCTATGCTATAGAT
                                  R  V  E  T  N  F  L  S  Y  A  I  D
2821  GATGCACAGAAATATCCATACCTTGCATCAATGGGCATTTATGTCTTCAAGAAAGATGCA
       D  A  Q  K  Y  P  Y  L  A  S  M  G  I  Y  V  F  K  K  D  A
2881  CTTTTAGACCTTCTCAAgtaatcacttcctgtgacttattctcatccaactcctagttt
       L  L  D  L  L  K
2941  acctttctaacagtgtcaattcttagGTCAAAATATACTCAATTACATGACTTTGGATCTG
                                   S  K  Y  T  Q  L  H  D  F  G  S
3001  AAATCCTCCCAAGAGCTGTACTAGATCATAGTGTGCAGgtaagtctgatctgtctggagt
       E  I  L  P  R  A  V  L  D  H  S  V  Q
3061  atgtgtctgtaaactgtaaattcttcatgtcaaaaagttgttttgttccagtttcca
3121  ctaccaatgcacgattatgtattctgcttccatgcatcatacatactaacaatacatt
3181  ttacgtattgttaggCATGGCTATTTTACGGGCTATTGGGAGGATGTTGAACAATCAA
                       A  C  I  F  T  G  Y  W  E  D  V  G  T  I  K
3241  ATCATTCTTTGATGCAAACTGGCCCTCACTGAGCAGgtactctgtcatgtattctgtac
```

FIG. 1D

```
             S  F  F  D  A  N  L  A  L  T  E  Q
3301  tgcatatatattacctggaattcaatgcatagaatgtgttagaccatcttagttccatcc
3361  tgttttcttcaattagcttatcattaatagtgttggctagaattaaacacaaattta
3421  cctaatatgtttctctcttcagCCTTCCAAGTTTGATTTTTACGATCCAAAACACCTTT
             P  S  K  F  D  F  Y  D  P  K  T  P  F
3481  CTTCACTGCACCCGATGCTTGCCTCCGACGCAATTGGACAAGTGCAAGtatatgtctt
       F  T  A  P  R  C  L  P  P  T  Q  L  D  K  C  K
3541  actgagcacaattgttacctgagcaagattttgtgtacttgactt gttctcctccacagA
3601  TGAAATATGCATTTATCTCAGATGGTTGCTTACTGAGAGAATGCAACATCGAGCATTCTG
       M  K  Y  A  F  I  S  D  G  C  L  R  E  C  N  I  E  H  S
3661  TGATTGGAGTCTGCTCACGTGTCAGTCTCTGGATGTGAACTCAAGtacatactctgccaa
       V  I  G  V  C  S  R  V  S  G  C  E  L  K
3721  tgtatctactcttgagtatataccattcaacaccaagcatcaccaaatcaccacagaacaat
3781  agcaacaaagcctttagttccaagcaatttaggtagccta gagttgaaatctaacaaa
3841  acaaaagtcaaagctctatcacgtggatagttgttttccatgcactcttatttaagctaa
3901  ttttttgggtatactacatccatttaatcatactgcactagtgtcttttgctcctttc
3961  cccattactatcgcgtcttaagatcatacgcactagtgtcttttagaggtctctggt
4021  ggacatgttcaaaccatccaatcggtcttggacaagttttcttgaatttgtgctacac
4081  ctaacctatcacgtatgtcatcgtttcaaactcgatcctcctgtatcatcataaatcca
4141  atgcaacatacgcatttatgcaacatttatctgttgaacatgtcatctttttgtaggtta
4201  acattatgcaccatacaatgtagcatgtctaatcatcatcataaaattacatttta g
4261  cttatgtggtatcctcttgccacttagaacaccatatgttgatgccatttcatccaccc
4321  tgctttgattctatggctaacatcttcattaatatcctcgcctctctgtatcattggtcc
```

FIG. 1E

```
4381  taaatatgaaatacattctttctggcactacttgaccttccaaactaacgtctccttt
4441  gctccttctgtgtgtagtagtaccgaagtcacatctcatatattcggtttagttcta
4501  ctaagtcccgggttcgatcccctcaggggtgaatttcgggcttgtaaaaaatcccc
4561  tcgctgtgtcccgcccgctctcggggatcgatatcctgcgcgcaccctccggctggca
4621  ttgcagagtgagcagttgatcggctcgttagtgatgggagcggggttcaagggttttct
4681  cggccgggaccatgttccggtctcttaatataatgccgggagggcagtcttccctcccc
4741  ggtcgagttttagttctactccgagtctaaaacctttggactctagagtccctgtcacaac
4801  tcacaactctagttttctattctacttctaccagcgttattaatgatcactatcgtc
4861  tgtaaaagcatacaccaatgtaatccccttgtatgtccttgtaatattatccatcaca
4921  agaaaaaaggtaaggctcaaagttgactttgatatagtcacaaaatttttgtacatgttcttaa
4981  atctgtatctcgtctcttgttcgaacactagtcataagccctcatcaagtcaatgaaaat
5041  tgagtccaacgtaatattccttgatatattttgtcattactgtctccatcttgtctcattaagaaaat
5101  cacgtgtaggtcctcattgtcctttgttcctatactgtccatcacacagaagttgttcctttttt
5161  ctctctcatagttaaccttttggcatgaaacaaaatcacacagaaggatctggatcccctgacaggtttatcaa
5221  taagatcccacacaaaagaggtttgatctaaggaatattcctccagcttcttgttactgtagtattgatgtaatat
5281  aatcctttgtgtttttcttaaaactgaatattccctgttcttgttgttacccccccccccc
5341  tcaatctgtttagcaagtgaacatgaaccacacctggttcttgttattgttattgcgcttctgataac
5401  cccccccgaggccccagatgaccagattaccacgacatgttattgttattgcgcttctgataac
5461  gtttgttgtactgttgaaaatcggtgacaattcattgttattgcgcttctgataac
5521  gacagGACTCCGTGATGATGGGAGCGGACACCTATGAACTGAAGAAGAAGCTTCAAAGC
        D   S   V   M   M   G   A   D   T   Y   E   T   E   E   A   S   K
5581  TACTGTTAGCTGGGAAGGTCCCAGTTGGAATAGGAAGGAACACAAAGATAAGgtgagtat
        L   L   A   G   K   V   P   V   G   I   G   R   N   T   K   I   R
5641  ggatgtgaaccaccggttagttcccaaaatatcactcactgatacctgatggtatcct
```

FIG. 1F

```
5701  ctgattatttcagGAACTGTATCATTGACATGAATGCTAGGATTGGGAAGAACGTGGTG
                  N  C  I  I  D  M  N  A  R  I  G  K  N  V  V 5761  ATCACAAACAGTAAGgtgagcgagccgcacctacatgggtgcagaatcttgtgtctcatc
       I  T  N  S  K 5821  tatcctaattcggtaattcctatccagcgctagtcttgtgaccatgggcatgggttcga 5881  ctctgtgacagGGCATCATCCAAGAGGCTGATCACCCCGAAGAAGGTACTACATAAGGTCTG
                  G  I  Q  E  A  D  H  P  E  E  G  Y  Y  I  R  S 5941  GAATCGTGGTGATCTTGAAGAATGCAACCATCAACGATGGGTCTGTCATATAGATCGGCT
       G  I  V  V  I  L  K  N  A  T  I  N  D  G  S  V  I  -

6001  GCGTGTGCGTCTACAAAACAAGAACCTACAAAGTCCGCTTGACAGAAAGTGCTTGTAACCT

6061  TGGTATGGTAAGAGCCGCTTGACAGAAAGTGCTTGGGCAAGATGCGTAGTCTGGC

6121  ATGCTGTTCCTTGACCATTGTGCTAGTATGTTATGTGCTAGTATGTGCCCTAGAAGTT

6181  GCAGCAAACCTTTTTATGAACCTTTGTATTCCATTACCTGCTTTGGATCAACTATATCT

6241  GTCATCCTATATATTACTAAATTTTTACGTGTTTTTCTAATTCGGTGTGCTGCTTTTGGGAT
```

FIG. 1G

MUTANT GENES ENCODING PLANT ADP-GLUCOSE PYROPHOSPHORYLASE AND METHODS OF USE

The subject invention was made with government support under a research project supported by National Science Foundation Grant No. IBN-960416 and U.S. Department of Agriculture Grant No. 94001704. The government has certain rights in this invention.

BACKGROUND OF THE INVENTION

ADP-glucose pyrophosphorylase (AGP) catalyzes the conversion of ATP and α-glucose-1-phosphate to ADP-glucose and pyrophosphate. ADP-glucose is used as a glycosyl donor in starch biosynthesis by plants and in glycogen biosynthesis by bacteria. The importance of ADP-glucose pyrophosphorylase as a key enzyme in the regulation of starch biosynthesis was noted in the study of starch deficient mutants of maize (Zea mays) endosperm (Tsai and Nelson, 1966; Dickinson and Preiss, 1969). AGP enzymes have been isolated from both bacteria and plants. Bacterial AGP consists of a homotetramer, while plant AGP from photosynthetic and non-photosynthetic tissues is a heterotetramer composed of two different subunits. The plant enzyme is encoded by two different genes, with one subunit being larger than the other. This feature has been noted in a number of plants. The AGP subunits in spinach leaf have molecular weights of 54 kDa and 51 kDa, as estimated by SDS-PAGE. Both subunits are immunoreactive with antibody raised against purified AGP from spinach leaves (Copeland and Preiss, 1981; Morell et al., 1987). Immunological analysis using antiserum prepared against the small and large subunits of spinach leaf showed that potato tuber AGP is also encoded by two genes (Okita et al., 1990). The cDNA clones of the two subunits of potato tuber (50 and 51 kDa) have also been isolated and sequenced (Muller-Rober et al., 1990; Nakata et al., 1991).

As Hannah and Nelson (Hannah and Nelson, 1975 and 1976) postulated, maize endosperm ADP-glucose pyrophosphorylase is encoded by two unlinked genes, Shrunken-2 (Sh2) (Bhave et al., 1990) and Brittle-2 (Bt2) (Bae et al., 1990). Sh2 and Bt2 encode the large subunit and small subunit of the enzyme, respectively. From cDNA sequencing, Sh2 and Bt2 proteins have predicted molecular weight of 57,179 Da (Shaw and Hannah, 1992) and 52,224 Da, respectively. The endosperm is the site of most starch deposition during kernel development in maize. Sh2 and bt2 maize endosperm mutants have greatly reduced starch levels corresponding to deficient levels of AGP activity. Mutations of either gene have been shown to reduce AGP activity by about 95% (Tsai and Nelson, 1966; Dickinson and Preiss, 1969). Furthermore, it has been observed that enzymatic activities increase with the dosage of functional wild type Sh2 and Bt2 alleles, whereas mutant enzymes have altered kinetic properties. AGP is the rate limiting step in starch biosynthesis in plants. Stark et al. placed a mutant form of E. coli AGP in potato tuber and obtained a 35% increase in starch content (Stark, 1992).

The cloning and characterization of the genes encoding the AGP enzyme subunits have been reported for various plants. These include Sh2 cDNA (Bhave et al., 1990), Sh2 genomic DNA (Shaw and Hannah, 1992), and Bt2 cDNA (Bae et al., 1990) from maize; small subunit cDNA (Anderson et al., 1989) and genomic DNA (Anderson et al., 1991) from rice; and small and large subunit cDNAs from spinach leaf (Morell et al., 1987) and potato tuber (Muller-Rober et al., 1990; Nakata et al., 1991). In addition, cDNA clones have been isolated from wheat endosperm and leaf tissue (Olive et al., 1989) and Arabidopsis thaliana leaf (Lin et al., 1988).

While introns in nuclear genes are ubiquitous in nature, the signals required to precisely define and recognize exon-intron borders are not fully understood. Studies from all eukaryotes point to splicing as being essentially a two-step cleavage-ligation reaction. The first step involves the cleavage at the 5' splice site that leads to the formation of an intron lariat with the adenosine residue of the branch point sequence located upstream to the 3' splice site. This is followed by the ligation of the exon and release of the intron lariat. (Moore and Sharp, 1993; Brown, 1996; Simpson and Filipowicz, 1996) This complex set of events is carried out by pre-mRNA association with a conglomeration of small nuclear RNA (snRNAs) and nuclear proteins that forms a dynamic large ribonucleosome protein complex termed a spliceosome (reviewed by Moore et al., 1993; Sharp, 1994). This fundamental process, common to all eurkaryotic gene expression, can have a diverse impact on the regulation of gene expression. For example, imprecise or inaccurate pre-mRNA splicing often imparts a mutant phenotype (reviewed by Weil and Wessler, 1990) whereas alternative splicing is sometimes important in the regulation of gene expression (Gorlach et al., 1995; Nishihama et al., 1997; Golovkin and Reddy, 1996). Interestingly, certain introns dramatically enhance gene expression in transient and stably transformed callus tissue (Callis et al., 1987; Clancy et al., 1994; Vasil et al., 1989). Finally, intron splicing is required for some plant viruses to be pathogenic (Kiss-Laszlo et al., 1995).

Unlike yeast and vertebrates, the lack of a plant in vitro system capable of efficiently splicing introns has hindered our understanding of the mechanism of splicing in plants. Despite the universal nature of the splicing pathway, primary transcripts of animal origin are not efficiently or accurately spliced in plants cells. Conversely, very few plant pre-mRNA are faithfully spliced in animal cells (Barta et al., 1986; van Santen and Spritz, 1987; Pautot et al., 1989). This species barrier between the heterologous splicing of pre-mRNA is also observed between monocots and dicots. Some monocot introns are not spliced in dicots (Keith and Chua, 1986; Goodall and Filipowicz, 1991). In contrast, introns of dicot origin are efficiently spliced in monocots, suggesting that monocot splicing machinery is more flexible or complex. There are also fundamental structural/sequence differences that differentiate plant introns from those of vertebrate and yeast introns (Goodall and Filipowicz, 1991; reviewed by Simpson and Filipowicz, 1996). Vertebrate introns possess a polypyramidine track and a somewhat conserved 3' sequence needed for lariat formation that is not found in plant introns (Simpson et al., 1996). A feature distinguishing plant introns from those of other organisms is their AU richness. This has been implicated to be essential for intron processing and for definition of the intron/exon junction (Lou et al., 1993; McCullough et al., 1993; Carle-Urioste et al., 1994; Luehrsen and Walbot, 1994). Interestingly, the requirement of AU rich region are more stringent in dicots than in monocots (Goodall and Filipowicz, 1989; 1991), and some monocot introns are, in fact, GC-rich.

Sweet corn is a major vegetable crop grown worldwide. Within the last twenty years the identification of a mutant allele of the shrunken-2 gene, termed sh2-R, was an important development for this crop. The advantage of the sh2-R gene is that it confers enhanced sweetness compared to older sweet corn varieties that do not contain the mutant form of the gene. Unfortunately, however, the use of this mutant form of the gene in corn also results in reduced germination and seedling vigor of the corn. Thus, there remains a need in the art for enhancing germination rate and/or seedling vigor in maize without negatively impacting the taste or sweetness of the corn. Improved growth characteristics would confer a major advantage in the commercial production of this corn.

BRIEF SUMMARY OF THE INVENTION

The subject invention concerns mutant alleles of the gene that encodes the large subunit of ADP-glucose pyrophosphorylase (AGP) in plants. These mutant polynucleotides, when expressed in a plant such as maize, provide for enhanced growth characteristics such as germination and seedling vigor, with little or no reduction in food or taste quality of vegetables or fruit from these plants. The mutant polynucleotides of the subject invention comprise a substitution of the wild-type terminal base in an intron from a G to another base, such as A, C or T. In one embodiment, the Shrunken-2 gene of maize contains a G to A mutation of the terminal nucleotide of an intron, thereby changing the AG nucleotide sequence that is found at the terminus of most plant gene introns to an AA sequence. In an exemplified embodiment, the mutation occurs in intron 2 of the Shrunken-2 gene.

The subject invention also concerns plants that have incorporated and express the polynucleotides of the invention that encode an AGP polypeptide.

The subject invention also concerns methods for enhancing growth characteristics of plants such as corn while maintaining the food quality of the vegetables or fruit produced form these plants. In one embodiment, the method comprises inserting in a plant genome a polynucleotide of the subject invention that encodes an AGP polypeptide.

BRIEF DESCRIPTION OF THE DRAWINGS

FIG. 1 shows the genomic nucleotide sequence of a wild-type Shrunken-2 allele of *Zea mays*. Introns are indicated by lower case letters. Base number 1 is the transcription start site. The arrow indicates the 3'-end of cDNA. Putative TATA, RY dyad and enhancer sequences are underlined.

In FIGS. 2A–2C, total endosperm RNA from wild-type and mutant sh2-i were subjected to RT-PCR using primers spanning exon 1–4 of Sh2 transcript. FIG. 2A depicts the resultant RT-PCR products resolved on a 1% agarose gel and stained with ethidium bromide. Lanes 1 and 2 represent the RT-PCR product derived from Sh2 and mutant sh2-i respectively. FIGS. 2B and 2C are DNA blots of the agarose gel probed with radiolabelled full length Sh2 cDNA and Sh2 exon 3 specific probes, respectively. FIG. 2D shows the schematic structure of the RT-PCR products derived from the mutant sh2-i and the wild-type Sh2 transcripts. Transcript sources are labelled at the left side of the panel; the numbers on the right side give the size and the relative proportion (%) of each transcript in the mutant endosperm. Arrows represent primers used for PCR amplification. Exons are represented by boxes.

BRIEF DESCRIPTION OF THE SEQUENCES

Figures 2A, 2B, 2C:
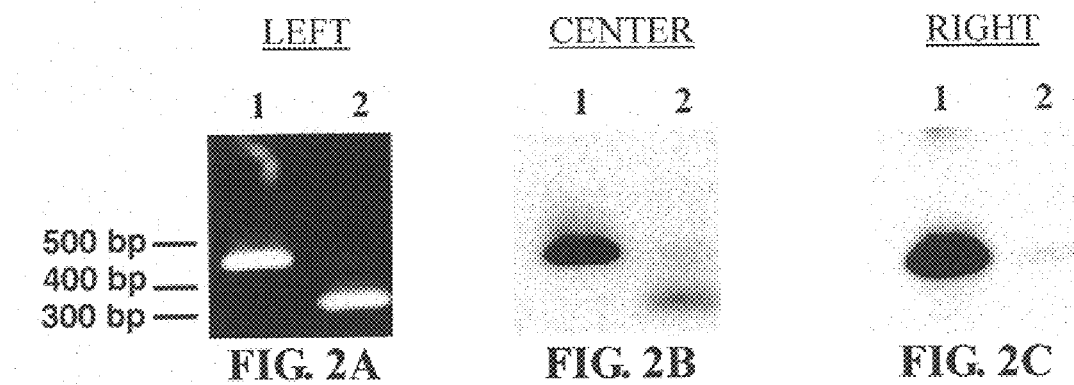
FIGS. 2A–2D show RT-PCR analysis of mutant sh2-i transcripts.

SEQ ID NO. 1 is the genomic nucleotide sequence of a wild-type Shrunken-2 allele of *Zea mays*.

DETAILED DESCRIPTION OF THE INVENTION

The subject invention concerns mutant alleles of the gene that encodes the large subunit of ADP-glucose pyrophosphorylase (AGP) in plants. These mutant polynucleotides, when expressed in a plant such as maize, provide for enhanced growth characteristics (e.g., germination and seedling vigor) without reduction in quality (e.g., taste) of vegetables or fruit from these plants. The mutant polynucleotides of the subject invention comprise a substitution of the wild-type terminal base in an intron from a G to another base, such as A, C or T. In one embodiment, the Shrunken-2 gene of maize contains a G to A mutation of the terminal nucleotide of an intron, thereby changing the AG nucleotide sequence that is found at the terminus of most plant gene introns to an AA sequence. In a preferred embodiment, the mutation occurs in intron 2 of the Shrunken-2 gene.

In an exemplified embodiment, the subject invention concerns the identification of a mutant form of the shrunken-2 allele, termed sh2-i, which results in greatly enhanced germination characteristics but without any decrease in eating quality (i.e., sweetness) as compared to commercially available corn that has been bred to express the sh2-R allele. The molecular lesion of the sh2-i allele has been identified in the subject invention. Specifically, the sh2-i allele, as compared to the wild-type Shrunken-2 allele, has undergone a G to A mutation at the terminal base of intron 2 in the maize gene.

The nucleotide mutations of introns contemplated within the scope of the subject invention can also be associated with or used in conjunction with other mutations of the genes encoding plant AGP polypeptide. These other mutations include, but are not limited to, mutations in the wild-type sequence that confer increased seed weight, heat stability, and other desirable characteristics in a plant expressing these mutant alleles. Specifically contemplated for use with the subject invention are those mutant alleles described in published International applications WO 98/10082 and WO 98/22601, herein incorporated by reference.

A mutation of the terminal nucleotide of intron 2 of the Shrunken-2 genomic nucleotide sequence is specifically exemplified herein. However, mutations of the terminal nucleotide in other Shrunken-2 introns are also within the scope of the invention as long as these confer substantially the same characteristics to a plant expressing the allele as those associated with the mutation at intron 2, i.e., germination and seedling vigor comparable to or better than plants expressing wild-type Shrunken-2 but with enhanced food or taste quality of the vegetable comparable to or better than that associated with mutants that provide enhanced sweetness, such as the Sh2-R allele, over wild-type. Another shrunken-2 mutant, containing a G to A substitution in the terminus of intron 12, did not exhibit the leaky phenotype nor the alternative RNA splicing events observed with sh2-i. Accordingly, this mutant was not expected to provide the enhanced eating quality associated with expression of sh2-i allele in sweet corn. The skilled artisan, having the benefit of the teachings of the present invention, can readily prepare mutations in other introns of the gene and determine whether the mutated introns confer the desired characteristics.

The polynucleotides of the present invention comprise an intron from an AGP-encoding gene wherein that intron comprises a nucleotide sequence in which the terminal nucleotide of the intron in the acceptor site is A, C, T, or modified variants thereof, and is not the wild-type G nucleotide. Preferably, the terminal nucleotide is an A, thereby providing the intron with an AA sequence at the 3' terminus of the intron. In an exemplified embodiment, a polynucleotide of the present invention comprises intron 2 of the shrunken-2 gene of maize wherein the AG nucleotide sequence at the terminus of intron 2 has been changed to AA. However, as noted above, mutated introns where the 3'-terminal nucleotide sequence is AC or AT are also contemplated in the present invention. It should also be understood that deletions, additions, and substitutions of the nucleotide sequence of the subject intron are contemplated within the scope of the present invention so long as the intron confers substantially the same phenotype and characteristics observed with the exemplified intron 2 of the sh2-i allele. Consensus sequences for the 5'- and 3'- ends of plant introns have been described (Brown, J. W. S. et al., 1996).

Plants, and large subunit AGP-encoding genes therefrom, contemplated within the scope of the invention include, for example, maize, corn, sweet peas, tomatoes and any other plant where high sucrose content of the vegetable or fruit is a desired characteristic.

The subject invention also concerns plants that have incorporated and express the polynucleotides of the invention that encode an AGP polypeptide. Included within the scope of the invention are maize, corn, sweet peas, tomato, banana and others where high sugar content is desired. In an exemplified embodiment, the plant is sweet corn. Polynucleotides of the present invention can be incorporated into selected plant genomes using standard techniques known in the art. Also contemplated within the scope of the invention is plant material, such as plant tissue, cells or seeds, that comprise a polynucleotide of the invention.

The subject invention also concerns methods for enhancing growth characteristics of plants such as corn while maintaining the food quality of the vegetables or fruit produced form these plants. In one embodiment, the method comprises inserting in a plant genome a polynucleotide of the subject invention that encodes an AGP polypeptide.

All publications cited herein are hereby incorporated by reference.

Materials and Methods

RNA and Genomic DNA Isolation Total RNA from the 20–22 day post pollination (dpp) kernels and leaf genomic DNA were isolated as described (Giroux et al., 1994; McCarty, 1986). RNA from suspension cells was extracted using TRIZOL Reagent (Life Technologies, Gaithersburg, Md.) according to the protocol of the manufacturer. Northern analysis was performed as described in Maniatis et al., (1993). Band intensities were measured by an IS-i 000 digital imaging system (Alpha Innotech Cooperation, San Leandro, Calif.).

PCR Amplification and Cloning Reverse Transcription Polymerase Chain Reaction (RT-PCR) was used to synthesize the full-length cDNA clones of sh2-i and sh2-7460 alleles by using a Superscript Reverse Transcriptase kit (Life Technologies). First strand cDNA synthesis was primed with oligo dT primer from developing maize endosperm total RNA and full length clones were isolated by use of primers SH2F0.1(5'-CAAGATCACGTCGACAGGCAAGTG-3') and SH2.3 (5'-GGTTTGCTGCAGCTTCTAGGGC-3'). These are complementary to the 5' and 3' non-translated regions of Sh2 cDNA, respectively. Underlined sequences contain modified bases to incorporate restriction sites for Sal I and Pst I. The restriction sites were used to subsequently clone the amplified fragment into the corresponding restriction site of vector pBLUESCRIPT KS+.

To amplify cDNA spanning exon 1 to exon 4 from sh2-i, primers SH2F0.1 and SH2R0.1 (5'-GCCTGTAACATCCTCCTGCAGGT-3') were employed. The resulting products were separated on a 1% agarose gel and alkaline transferred onto a Hybond H+ membrane (Amersham International plc, Arlington Heights, Ill.), according to the protocol provided by the manufacturer. This blot was first probed with exon 3 specific probe according to the procedure described by Church and Gilbert (1984). Exon 3 specific probe was generated by polymerase chain reaction (PCR) amplification of Sh2 cDNA using primers SH2LHS1 (5'-CATTCTCAAACACAGTCGACTAG-3') and SH2LHSR (5'-AGCAGGCGCAGCTCTAG-3'). The blot was then washed twice with 2X SSPE/0.1% SDS and 0.2X SSPE/0.1% SDS at 65° C. for 20 min, and then subjected to overnight exposure to X-ray film to monitor the efficacy of probe removal. It was then probed with full length Sh2 cDNA. Resulting autoradiograms were quantified by a Phosphoimager (Molecular Dynalics, Sunnyvale, Calif.) or with an IS-1000 Digital Imaging System (Alpha Innotech Corporation).

Genomic sequences from exon 1 to exon 4 were amplified using primers SH2F0.1 and SH2R0.1 (5'GCCTGTAACATCCTCCTGCAGGT 3') using leaf DNA as template. Similarly, exon 7 to exon 14 of mutant sh2-7460 was amplified using primers, SHLH872 (5'-ACATGTCGACGATGCTGCTGCTATC-3') and SHLH871R (5'-GAGTTCACCTGCAGAGCTGAC-3'). Resulting fragments were cloned into pBLUESCRIPT KS+ or pUC 19. DNA sequencing was done at the University of Florida DNA Sequencing Core Laboratory, using ABI Prism Dye Terminator sequencing protocol developed by Applied Biosystems. DNA sequence derived from the mutants were compared to the Sh2 sequence (Shaw and Hannah, 1992) using a DNA analysis software DNA-Star (Lasergen Inc., Madison, Wis.).

Bacterial Expression of AGP The E. coli expression (Iglesias et al., 1993) was employed to monitor sh2-i transcripts for functional AGP activity. Full-length Sh2 transcript from wild type and the smaller transcript of mutant sh2-i were RT-PCR amplified using primers LH377 (5'-GGGGCCATGGCCCAGTTTGCACTTGCATTGGACG ACACG-3') and LH396 (5'-CCCCGAGCTCACTATATGACAGACCCATCGTTGA TGG-3') as described earlier, and cloned into the NcoI and SstJ restriction sites of bacterial expression vector pMSH (Iglesias et al., 1993). Resulting clones are termed pSHW and pMSHi, respectively. The low abundance of the larger sh2-i transcript and its close proximity following electrophoresis to the more abundant, smaller transcript made it difficult to effectively resolve the DNA bands. Hence, the exon 1 to exon 7 region of sh2-i transcripts was amplified using primers LH377 and 5H796R (5'-CTCTCATCAACAGGAGCA C-3'). This allowed for a definitive resolution of fragments of~600 and 700 bp on 1% agarose gel. The larger fragment of~700 bp of mutant sh2-i was eluted from the gel, restricted with NcoI and XhoI and cloned into the corresponding site of pMS Hi replacing the corresponding sequence in the smaller transcript, giving rise to pMSHWi. Constructs were separately transformed into an E. coli strain AC70R-504 lacking an endogenous AGP activity, but harboring the Bt2 gene on the compatible vector described by Giroux et al. (1996). Transformed cells were grown for 16 hours on LB plates containing 1% glucose and then iodine stained to monitor ADP glucose pyrophosphorylase (AGP) activity as described earlier (Iglesias et al., 1993; Greene et al., 1996).

Particle Bombardment and Expression Vectors Maize cell line PC5, established from mesocotyl tissue of germinating seed (Chourey and Zurawski, 1981) was cultured in a liquid MS media supplemented with 2 mg/liter 2, 4-D. Cells were grown in the dark at 27° C. on a shaker at 150 rpm and were routinely subcultured at 7 day intervals. After 3 days of subculture, 2 ml of cells were transferred onto a Whatman filter disc for particle bombardment. The disc was placed on a petri plate containing MS-Agarose media and used immediately as a target for the particle bomb. Preparation of the DNA/gold mixture and the parameters for bombardment were previously described (Taylor and Vasil, 1991). Bio-rad Laboratories, Hercules, Calif. (Model PDS-1 000/HE Biolistic Particle Delivery System) was used for bombardment. Cells were harvested 22 hr post bombardment, frozen in liquid nitrogen and stored at −70° C. for further analysis.

Exon 2 to exon 4 was isolated from 1 μg of leaf genomic DNA from wild type and sh2-i by 30 cycles of PCR amplification using primers 5H2F0.1 and SH2R0.1. Resulting 1.6 kb fragments were blunt ended with Pfu Polymerase~ew England Biolabs, Beverly, Mass.) and ligated into the solitary EcoRV site present in the luciferase coding region of the plant expression vector pAHC18 (Christensen and Quail, 1996). Resulting constructs were expressed in maize suspension cells. Total RNA extracted from the cells was treated with Amplification Grade DNAse I (BRL) and subjected to RT-PCR using primers (5'-CCCGGTTTTAAT GAATACGT-3') and LucUp.Pr2 (5'-CCGTGCTCCAAAA CAACAA-3'), that flanked the EcoRV site of the luciferase coding region. The resulting PCR fragments were blotted and probed with luciferase coding region of pAHC 18. The fragments were eluted from the gel and directly sequenced.

Following are examples which illustrate procedures for practicing the invention. These examples should not be construed as limiting. All percentages are by weight and all solvent mixture proportions are by volume unless otherwise noted.

EXAMPLE 1
Germination of sh2-i and Mutant and Characterization of AGP Activity The mutant sh2-i was generated by EMS mutagenesis and conditions an intermediate or leaky phenotype in comparison to virtually all other sh2 mutant alleles. To determine whether the detected diminutive SH2 protein conditioned AGP activity in sh2-i, the small transcript of sh2-i was cloned. Sequencing revealed that this transcript lacked exon 3. Exon 3 is a multiple of 3 (123 bp) in length, thus deletion of this exon maintains translational continuity.

The sh2-i transcript was cloned and co-expressed with the wild-type Brittle2 (Bt2) gene in an E.coli mutant lacking the endogenous bacterial AGP, glg-C (Igleasias et al., 1993). Expression of wild-type Sh2 and Bt2 genes complements the E.coli mutant giving rise to glycogen which can be visualized easily by exposure to iodine vapors. In contrast, expression of the abbreviated sh2-i transcript did not complement the glg-C mutant. We conclude from these experiments that the truncated sh2-i transcript does not encode the AGP activity encountered in this mutant and that an additional source of AGP must condition the leaky phenotype of this mutant.

EXAMPLE 2
Reverse Transcription PCR Analysis

Figure 2D:
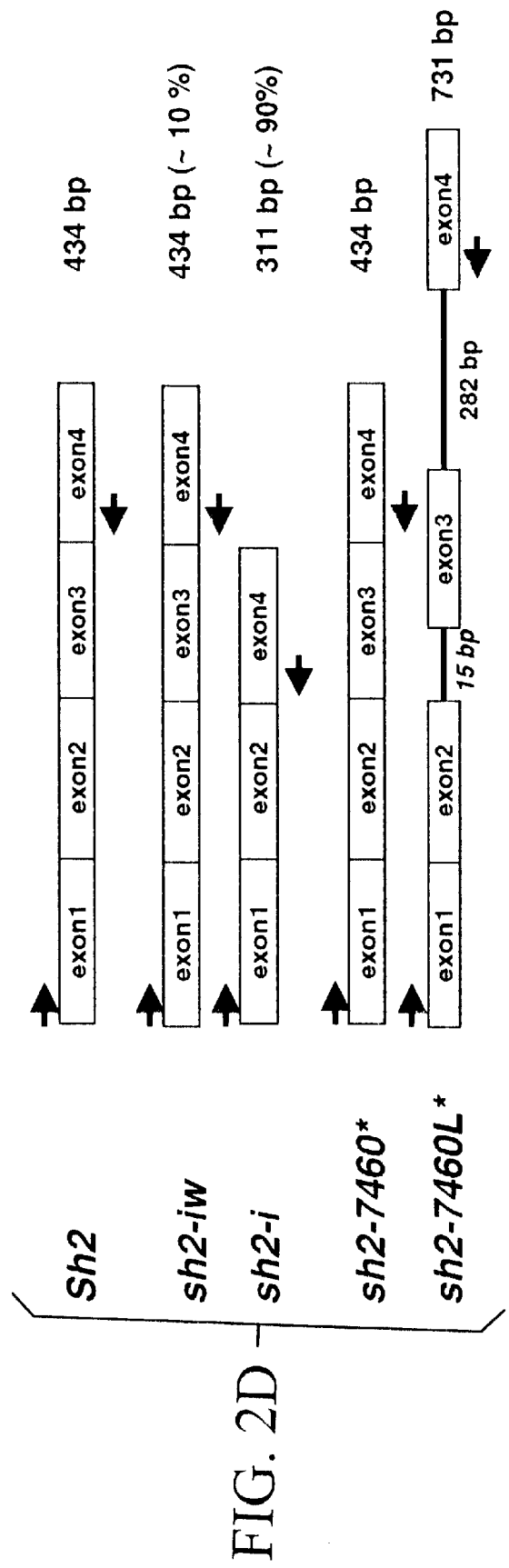

Reverse transcription PCR (RT-PCR) analysis was performed on oligo-dT primed first-strand cDNA from wildtype and sh2-i developing endosperm poly-A RNA using primers flanking exon 1 to exon 4. A low abundant, wild-type-sized PCR product from sh2-i (FIG. 2A, lane 2) was observed. This fragment hybridizes to a full length Sh2 cDNA probe (FIG. 2B, lane 2) as well as to a probe specific to exon 3 (FIG. 2C, lane 2). As judged by digital imaging, this fragment comprises approximately 10% of the total Sh2 transcript. Full-length clones comprising the larger transcript of sh2-i were isolated by PCR, sequenced and expressed in E.coli. Sequencing showed that this transcript contains a completely wild-type exon 3 perfectly abutting exons 2 and 4 (FIG. 2D). Expression of this transcript leads to a functional AGP. Thus, low levels of AGP activity found in sh2-i arise from this low abundant transcript.

EXAMPLE 3
Multiple RNA Splicing in sh2-i Mutant

Figure 3:
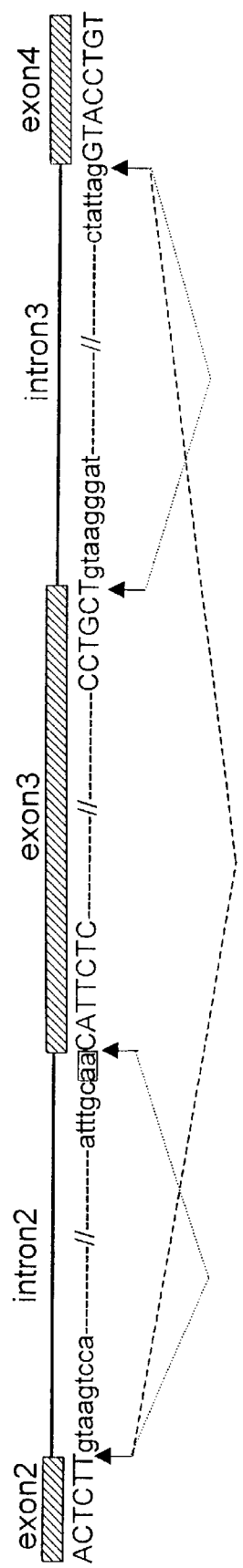
FIG. 3 shows a schematic representation of the genomic sequence bearing the splice site alterations of the mutant sh2-i (exon 1–4). The point mutation that altered the 3' splice site AG to AA of intron 2 in mutant sh2-i is boxed. Arrows joined by lines mark the donor and acceptor sites used during RNA splicing to generate the mutant transcripts.

Since two transcripts arise from one mutant gene, the sh2-i pre-RNA must undergo multiple splicing events. Primers spanning exon 1 to exon 4 were used to isolate sh2-i genomic DNA. Sequencing revealed that sh2-i harbors a G to A transition at the terminus of intron 2 (FIG. 3). Hence, loss of a wild-type splice site at the terminus of intron 2 leads to skipping of exon 3 in 90% of the processed transcripts. In these cases, splicing occurs between the donor site of intron 2 and the acceptor site of intron 3. In 10% of the transcripts, however, the intron 2 acceptor site functions in splicing even though it lacks the invariant AG terminus.

EXAMPLE 4
Incorporation of sh2-i Allele into Corn

The sh2-i allele was incorporated by crossing and five backcrosses into two inbreds containing the sh2-R allele. Visual inspection of early seedling growth revealed enhanced vigor in the sh2-i materials compared to their sh2-R counterparts in each of the backcross generations (a total of 10 observation sets). Following self-pollination, material homozygous for sh2-i was identified and $F_1$ hybrid seed between the two converted inbreds was made. These materials were grown, self-pollinated and harvested at the normal eating stage of 18 days post-pollination. Corresponding material containing the germination-inferior allele, sh2-R was handled in identical fashion. Corn ears were tasted without cooking immediately after harvest and after 7 days storage at 30° C. by 11 persons chosen at random. Differences in eating quality between the two genotypes could not be detected at 0 or 7 days following harvest. It appears that the germination-superior allele, sh2-i does not condition reduced eating quality compared to commercially-available materials.

It should be understood that the examples and embodiments described herein are for illustrative purposes only and that various modifications or changes in light thereof will be suggested to persons skilled in the art and are to be included within the spirit and purview of this application and the scope of the appended claims.

References

International PCT application, publication No. WO 98/10082

International PCT application, publication No. WO 98/22601

Anderson, J. M., J. Hnilo, R. Larson, t. W. Okita, M. Morell, J. Preiss (1989) The encoded primary sequence of a rice seed ADP-glucose pyrophosphorylase subunit and its homology to the bacterial enzyme. *J.Biol. Chem.* 264:12238–12242.

Anderson, J. M., R. Larsen, D. Laudencia, W. T. Kim, D. Morrow, T. W. Okita, J. Preiss (1991) Molecular characterization of the gene encoding a rice endosperm-specific ADP-glucose pyrophosphorylase subunit and its developmental pattern of transcription. *Gene* 97:199–205.

Bae, J. M., M. Giroux, L. C. Hannah (1990) Cloning and characterization of the Brittle-2 gene of maize. *Maydica* 35:317–322.

Barta, A., K. Sommergruber, D. Thompson, K. Harmuth, M. E. Matzke, A. J. M. Matzke (1986) The expression of nopaline synthase-human growth hormone chimaeric gene in transformed tobacco and sunflower callus tissue. *Plant Mol Biol.* 6: 347–357.

Bhave, M. R., S. Lawrence, C. Barton, L. C. Hannah (1990) Identification and molecular characterization of Shrunken-2 cDNA clones of maize. *Plant Cell* 2:581–588.

Brown, J. W. S. (1996) Arabidopsis intron mutations and pre-mRNA splicing. *Plant J.* 10:771–780.

Brown, J. W. S., P. Smith, C. G. Simpson (1996) *Plant Mol. Biol.* 32: 531–535.

Callis, J., M. Fromm, V. Walbot (1987) Introns increase gene expression in cultured maize cells. *Genes & Development* 1: 1183–1200.

Carle-Urioste, J. C., C. H. Ko, M. Benito, V. Walbot (1994) In vivo analysis of intron processing using splicing-dependent reporter gene assays. *Plant Mol. Biol.* 26: 1785–1795.

Clancy, M., V. Vasil, L. C. Hannah, I. K. Vasil (1994) Maize shrunken-1 intron and exon regions increase gene expression in maize protoplasts. *Plant Science* 98: 151–161.

Copeland, L., J. Preiss (1981) Purification of spinach leaf ADP-glucose pyrophosphorylase. *Plant Physiol.* 68:996–1001.

Dickinson, D. B., J. Preiss (1969) Presence of ADP-glucose pyrophosphorylase in Shrunken-2 and Brittle-2 mutants of maize endosperm. *Plant Physiol.* 44:1058–1062.

Giroux, M. J., C. Boyer, G. Feix, L. C. Hannah (1994) Coordinated transcriptional regulation of storage product genes in the maize endosperm. *Plant Physiol.* 106: 713–722.

Golovkin, M., A. S. Reddy (1996) Structure and expression of a plant U1 snRNP 70K gene: alternative splicing of U1 snRNP 70K pre-mRNAs produces two different transcripts. *Plant Cell* 8: 1421–1435.

Goodall, G. J., W. Filipowicz (1989) The AU-rich sequences present in the introns of plant nuclear pre-mRNAs are required for splicing. *Cell* 58: 473–483.

Goodall, G. J., W. Filipowicz (1991) Different effects of intron nucleotide composition and secondary structure on pre-mRNA splicing in monocot and dicot plants. *EMBO J.* 10: 2635–2644.

Gorlach, J., H-R. Raesecke, G. Abel, R. Wehrli, N. Amrhein, J. Schmid (1995) Organ-specific differences in the ratio of alternatively spliced chorismate synthase (LeCS2) transcripts in tomato. *Plant J.* 8: 451–456.

Hannah, L. C., O. E. Nelson (1975) Characterization of adenosine diphosphate glucose pyrophosphorylase from developing maize seeds. *Plant Physiol.* 55:297–302.

Hannah, L. C., O. E. Nelson (1976) Characterization of adenosine diphosphate glucose pyrophosphorylase from Shrunken-2 and Brittle-2 mutants of maize. *Biochem. Genet.* 14:547–560.

Iglesias, A. A., G. F. Barry, C. Myer, L. Bloksberg, P. A. Nakata, T. Greene, M. J. Laughlin, T. W. Okita, G. M. Kishore, J. Preiss (1993) Expression of the potato tuber ADP-glucose pyrophosphorylase in *Escherichia coli. J Biol. Chem.* 268: 1081–1086.

Keith, B., N-H. Chua (1986) Monocot and dicot pre-mRNAs are processed with different efficiencies in transgenic tobacco. *EMBO J.* 5: 2419–2425.

Kiss-Laszlo, Z., S. Blanc, T. Hohn (1995) Splicing of cauliflower mosaic virus 35S RNA is essential for viral infectivity. *EMBO J.* 14: 3552–3562.

Lin, T., T. Caspar, C. Somerville, J. Preiss (1988) A starch deficient mutant of *Arabidopsis thaliana* with low ADP-glucose pyrophosphorylase activity lacks one of the two subunits of the enzyme. *Plant Physiol.* 88:1175–1181.

Lou, H., A. J. McCullough, M. A. Schuler (1993) 3' splice site selection in dicot plant nuclei is position dependent. *Mol Cell. Biol.* 13: 4485–4493.

Luehrsen, K. R., Walbot, V. (1994) Intron creation and polyadenylation in maize are directed by AU-rich RNA. *Genes and Development* 8:1117–1130.

Maniatis, T., E. F. Fritsch, J. Sambrook (1989) *Molecular Cloning: A Laboratory Manual,* 2d Edition, Cold Spring Harbor Laboratory, Cold Spring Harbor, N.Y.

McCarty, D. R. (1986) A simple method for extration of RNA from maize tissue. *Maize Genet. Coop.* Newslett. 60: 61.

McCullough, A. J., H. Lou, M. A. Schuler (1993) Factors affecting authentic 5' splice site selection in plant nuclei. *Mol. Cell. Biol.* 13: 1323–1331.

Moore, M. J., P. A. Sharp (1993) Evidence of two active sites in the spliceosome provided by stereochemistry of pre-mRNA splicing. *Nature* 365: 364–368.

Moore, M. J., C. C. Query, P. A. Sharp (1993) Splicing of precursors to messenger RNAs by the spliceosome. In the *RNA World,* R. Gesteland and J. Atkins, eds. (Cold Spring Harbor Laboratory Press), pp 303–308.

Morell, M., M. Bloom, J. Preiss (1988) Affinity Labeling of the Allosteric Activator Site(s) of spinach leaf ADP-glucose pyrophosphorylase. *J Bio. Chem.* 263:633.

Muller-Rober, B. T., J. Kossmann, L. C. Hannah, L. Willmitzer, U. Sonnewald (1990) One of the two different ADP-glucose pyrophosphorylase genes from potato responds strongly to elevated levels of sucrose. *Mol. Gen. Genet.* 224:136–146.

Nakata, P. A., T. W. Greene, J. M. Anderson, B. J. Smith-White, T. W. Okita, J. Preiss (1991) Comparison of the primary sequences of two potato tuber ADP-glucose pyrophosphorylase subunits. *Plant Mol. Biol.* 17: 1089–1093.

Nishihama, R. H. Banno, E. Kawahara, K. Irie, Y. Machida (1997) Possible involvement of differential splicing in regulation of the activity of Arabidopsis ANPL that is related to mitogen-activated protein kinase kinase kinases (MAPKKKs). *Plant J.* 12: 39–48.

Okita, T. W., P. A. Nakata, J. M. Anderson, J. Sowokinos, M. Morell, J. Preiss (1990) The subunit structure of potato tuber ADP-glucose pyrophosphorylase. *Plant Physiol.* 93:785–790.

Olive, M. R., R. J. Ellis, W. W. Schuch (1989) Isolation and nucleotide sequences of cDNA clones encoding ADP-glucose pyrophosphorylase polypeptides from wheat leaf and endosperm. *Plant Physiol. Mol. Biol.* 12:525–538.

Pautot, V., R. Brzezinski, M. Tepfer (1989) Expression of a mouse metallothionein gene in transgenic plant tissue. *Gene* 77: 133–140.

Sharp, P. A. (1994) Split genes and RNA splicing. *Cell* 77: 805–815.

Shaw, J. R., L. C. Hannah (1992) Genomic nucleotide sequence of a wild type Shrunken-2 allele of *Zea Mays. Plant Physiol.* 98:1214–1216.

Simpson, G. G., G. Clark, D. Davidson, P. Smith, J. W. S. Brown (1996) Mutation of putative branchpoint consensus sequences in plant introns reduces splicing efficiency. *Plant J.* 9: 369–380.

Simpson, G. G., W. Filipowicz (1996) Splicing of precursors to mRNA in higher plants: mechanism, regulation and sub-nuclear organisation of the spliceosomal machinery. *Plant. Mol. Biol.* 32: 1–41.

Stark, et al. (1992) Regulation of the amount of starch in plant tissues by ADP-glucose pyrophosphorylase. *Science* 258:287.

Tsai, C., O. E. Nelson (1966) Starch-deficient maize mutant lacking adenosine diphosphate glucose pyrophosphorylase activity. *Science* 151:341–343.

van Santen, V. L., R. A. Spritz (1987) Splicing of plant pre-mRNAs in animal systems and vice versa. *Gene* 56: 253–265.

Vasil, V., M. Clancy, R. J. Ferl, I. K. Vasil, L. C. Hannah (1989) Increased gene expression by the first intron of maize shrunken-1 locus in grass species. *Plant Physiol.* 91:1575–1579.

Weil, C. F., S. R. Wessler (1990) The effects of plant transposable element insertion on transcription initiation and RNA processing. *Ann. Rev. Plant. Physiol. Plant Mol. Biol.* 41: 527–552.

What is claimed is:

1. A polynucleotide molecule that encodes a large subunit of plant ADP-glucose pyrophosphorylase, wherein said polynucleotide comprises the genomic nucleotide sequence of the Shrunken-2 gene of maize, wherein said gene comprises intron 2, and wherein said Shrunken-2 gene comprises a substitution of the wild-type terminal nucleotide of intron 2 of said gene from a G to an A.

2. The polynucleotide according to claim 1, wherein said wild-type genomic nucleotide sequence of said Shrunken-2 gene has the sequence shown in SEQ ID NO. 1, wherein said nucleotide sequence of SEQ ID NO. 1 has been modified by a substitution of the terminal nucleotide of intron 2 from a G to an A.

3. A polynucleotide molecule comprising an intron of the Shrunken-2 gene of maize, wherein said intron is intron 2 of said Shrunken-2 gene and wherein said intron comprises a substitution of the wild-type terminal nucleotide from a G to an A.

4. A plant or plant material each comprising a genome, wherein a polynucleotide of claim 1 as been incorporated into said genome.

5. The plant according to claim 4, wherein said plant is maize.

6. A method for enhancing growth characteristics of a food plant where high sucrose content is desired, without a decrease in food quality of said plant, said method comprising incorporating, a polynucleotide of claim 1 into a plant genome.

7. The method according to claim 6, wherein said plant is maize.

* * * * *

UNITED STATES PATENT AND TRADEMARK OFFICE
CERTIFICATE OF CORRECTION

PATENT NO. : 6,184,438 B1
DATED : February 6, 2001
INVENTOR(S) : L. Curtis Hannah It is certified that error appears in the above-identified patent and that said Letters Patent is hereby corrected as shown below:

Column 1,
Line 48, "bt2" should read -- Bt2 --.

Column 3,
Line 30, "form" should read -- from --.
Line 61, "AG to AA" should read -- A<u>G</u> to A<u>A</u> --.

Column 5,
Line 36, "form" should read -- from --.
Line 50, "Cooperation" should read -- Corporation --.
Line 60, "CAAGATCACGTCGACAGGCAAGTG" should read
-- CAAGATCAC<u>G</u>TCG<u>AC</u>AGGCAAGTG --.

Column 6,
Line 19, "Dynalics" should read -- Dynamics --.
Line 24, "5' GCCTGTAACATCCTCCTGCAGGT 3'" should read
-- 5' GCCTGTAACATCCTCC<u>T</u>GCAGGT 3' --.
Line 28, "GAGTTCACCTGCAGAGCTGAC" should read
-- GAGTTCAC<u>C</u>TGCAGAGCTGAC --.
Line 46, "SstJ" should read -- Sst I --.
Line 58, "pMS Hi" should read -- pMSHi --.

Column 7,
Line 46, "SH2" should read -- Sh2 --.
Line 53, "Igleasias" should read -- Iglesias --.

Column 8,
Line 44, "30°C" should read -- 3°C --.
Line 63, "t. W." should read -- T. W. --.

UNITED STATES PATENT AND TRADEMARK OFFICE
CERTIFICATE OF CORRECTION

PATENT NO. : 6,184,438 B1
DATED : February 6, 2001
INVENTOR(S) : L. Curtis Hannah It is certified that error appears in the above-identified patent and that said Letters Patent is hereby corrected as shown below:

<u>Column 10,</u>
Line 47, "ANPL" should read -- ANP1 --.

Signed and Sealed this

Fourteenth Day of May, 2002

*Attest:*

JAMES E. ROGAN
*Attesting Officer*  *Director of the United States Patent and Trademark Office*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 7739 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TAAGAGGGGT GCACCTAGCA TAGATTTTTT GGGCTCCCTG GCCTCTCCTT TCTTCCGCCT      60

GAAAACAACC TACATGGATA CATCTGCAAC CAGAGGGAGT ATCTGATGCT TTTTCCTGGG     120

CAGGGAGAGC TATGAGACGT ATGTCCTCAA AGCCACTTTG CATTGTGTGA AACCAATATC     180

GATCTTTGTT ACTTCATCAT GCATGAACAT TTGTGGAAAC TACTAGCTTA CAAGCATTAG     240

TGACAGCTCA GAAAAAAGTT ATCTCTGAAA GGTTTCATGT GTACCGTGGG AAATGAGAAA     300

TGTTGCCAAC TCAAACACCT TCAATATGTT GTTTGCAGGC AAACTCTTCT GGAAGAAAGG     360

TGTCTAAAAC TATGAACGGG TTACAGAAAG GTATAAACCA CGGCTGTGCA TTTTGGAAGT     420

ATCATCTATA GATGTCTGTT GAGGGGAAAG CCGTACGCCA ACGTTATTTA CTCAGAAACA     480

GCTTCAACAC ACAGTTGTCT GCTTTATGAT GGCATCTCCA CCCAGGCACC CACCATCACC     540

TATTCACCTA TCTCTCGTGC CTGTTTATTT TCTTGCCCTT TCTGATCATA AAAAATCATT     600

AAGAGTTTGC AAACATGCAT AGGCATATCA ATATGCTCAT TTATTAATTT GCTAGCAGAT     660

CATCTTCCTA CTCTTTACTT TATTTATTGT TTGAAAAATA TGTCCTGCAC CTAGGGAGCT     720

CGTATACAGT ACCAATGCAT CTTCATTAAA TGTGAATTTC AGAAAGGAAG TAGGAACCTA     780

TGAGAGTATT TTTCAAAATT AATTAGCGGC TTCTATTATG TTTATAGCAA AGGCCAAGGG     840

CAAAATCGGA ACACTAATGA TGGTTGGTTG CATGAGTCTG TCGATTACTT GCAAGAAATG     900

TGAACCTTTG TTTCTGTGCG TGGGCATAAA ACAAACAGCT TCTAGCCTCT TTTACGGTAC     960

TTGCACTTGC AAGAAATGTG AACTCCTTTT CATTTCTGTA TGTGGACATA ATGCCAAAGC    1020

ATCCAGGCTT TTTCATGGTT GTTGATGTCT TTACACAGTT CATCTCCACC AGTATGCCCT    1080

CCTCATACTC TATATAAACA CATCAACAGC ATCGCAATTA GCCACAAGAT CACTTCGGGA    1140

GGCAAGTGTG ATTTCGACCT TGCAGCCACC TTTTTTTGTT CTGTTGTAAG TATACTTTCC    1200

CTTACCATCT TTATCTGTTA GTTTAATTTG TAATTGGGAA GTATTAGTGG AAAGAGGATG    1260

AGATGCTATC ATCTATGTAC TCTGCAAATG CATCTGACGT TATATGGGCT GCTTCATATA    1320
```

```
ATTTGAATTG CTCCATTCTT GCCGACAATA TATTGCAAGG TATATGCCTA GTTCCATCAA    1380

AAGTTCTGTT TTTTCATTCT AAAAGCATTT TAGTGGCACG CAATTTTGTC CATGAGGGAA    1440

AGGAAATCTG TTTTGGTTAC TTTGCTTGAG GTGCATTCTT CATATGTCCA GTTTTATGGA    1500

AGTAATAAAC TTCAGTTTGG TCATAAGATG TCATATTAAA GGGCAAACAT ATATTCAATG    1560

TTCAATTCAT CGTAAATGTT CCCTTTTTGT AAAAGATTGC ATACTCATTT ATTTGAGTTG    1620

CAGGTGTATC TAGTAGTTGG AGGAGATATG CAGTTTGCAC TTGCATTGGA CACGAACTCA    1680

GGTCCTCACC AGATAAGATC TTGTGAGGGT GATGGGATTG ACAGGTTGGA AAAATTAAGT    1740

ATTGGGGGCA GAAAGCAGGA GAAAGCTTTG AGAAATAGGT GCTTTGGTGG TAGAGTTGCT    1800

GCAACTACAC AATGTATTCT TACCTCAGAT GCTTGTCCTG AAACTCTTGT AAGTATCCAC    1860

CTCAATTATT ACTCTTACAT GTTGGTTTAC TTTACGTTTG TCTTTTCAAG GGAAATTTAC    1920

TGTATTTTTT GTGTTTTGTG GGAGTTCTAT ACTTCTGTTG GACTGGTTAT TGTAAAGATT    1980

TGTTCAAATA GGGTCATCTA ATAATTGTTT GAAATCTGGG AACTGTGGTT TCACTGCGTT    2040

CAGGAAAAAG TGAATTATTG GTTACTGCAT GAATAACTTA TGGAAATAGA CCTTAGAGTT    2100

GCTGCATGAT TATCACAAAT CATTGCTACG ATATCTTATA ATAGTTCTTT CGACCTCGCA    2160

TTACATATAT AACTGCAACT CCTAGTTGCG TTCAAAAAAA AAAATGCAAC TCTTAGAACG    2220

CTCACCAGTG TAATCTTTCC TGAATTGTTA TTTAATGGCA TGTATGCACT ACTTGTATAC    2280

TTATCTAGGA TTAAGTAATC TAACTCTAGG CCCCATATTT GCAGCATTCT CAAACACAGT    2340

CCTCTAGGAA AAATTATGCT GATGCAAACC GTGTATCTGC TATCATTTTG GGCGGAGGCA    2400

CTGGATCTCA GCTCTTTCCT CTGACAAGCA CAAGAGCTAC GCCTGCTGTA AGGGATAACA    2460

CTGAACATCC AACGTTGATT ACTCTATTAT AGTATTATAC AGACTGTACT TTTCGAATTT    2520

ATCTTAGTTT TCTACAATAT TTAGTGGATT CTTCTCATTT TCAAGATACA CAATTGATCC    2580

ATAATCGAAG TGGTATGTAA GACAGTGAGT TAAAAGATTA TATTTTTGG GAGACTTCCA    2640

GTCAAATTTT CTTAGAAGTT TTTTGGTCC AGATGTTCAT AAAGTCGCCG CTTTCATACT    2700

TTTTTTAATT TTTTAATTGG TGCACTATTA GGTACCTGTT GGAGGATGTT ACAGGCTTAT    2760

TGATATCCCT ATGAGTAACT GCTTCAACAG TGGTATAAAT AAGATATTTG TGATGAGTCA    2820

GTTCAATTCT ACTTCGCTTA ACCGCCATAT TCATCGTACA TACCTTGAAG GCGGGATCAA    2880

CTTTGCTGAT GGATCTGTAC AGGTGATTTA CCTCATCTTG TTGATGTGTA ATACTGTAAT    2940

TAGGAGTAGA TTTGTGTGGA GAGAATAATA AACAGATGCC GAGATTCTTT TCTAAAAGTC    3000

TAGATCCAAA GGCATTGTGG TTCAAAACAC TATGGACTTC TACCATTTAT GTCATTACTT    3060

TGCCTTAATG TTCCATTGAA TGGGGCAAAT TATTGATTCT ACAAGTGTTT AATTAAAAAC    3120

TAATTGTTCA TCCTGCAGGT ATTAGCGGCT ACACAAATGC CTGAAGAGCC AGCTGGATGG    3180

TTCCAGGGTA CAGCAGACTC TATCAGAAAA TTTATCTGGG TACTCGAGGT AGTTGATATT    3240

TTCTCGTTTA TGAATGTCCA TTCACTCATT CCTGTAGCAT TGTTTCTTTG TAATTTTGAG    3300

TTCTCCTGTA TTTCTTTAGG ATTATTACAG TCACAAATCC ATTGACAACA TTGTAATCTT    3360

GAGTGGCGAT CAGCTTTATC GGATGAATTA CATGGAACTT GTGCAGGTAT GGTGTTCTCT    3420

TGTTCCTCAT GTTTCACGTA ATGTCCTGAT TTTGGATTAA CCAACTACTT TTGGCATGCA    3480

TTATTTCCAG AAACATGTCG AGGACGATGC TGATATCACT ATATCATGTG CTCCTGTTGA    3540

TGAGAGGTAA TCAGTTGTTT ATATCATCCT AAATATGAATA TGTCATCTTG TTATCCAACA    3600

CAGGATGCAT ATGGTCTAAT CTGCTTTCCT TTTTTTTCCC TTCGGAAGCC GAGCTTCTAA    3660
```

-continued

```
AAATGGGCTA GTGAAGATTG ATCATACTGG ACGTGTACTT CAATTCTTTG AAAAACCAAA     3720

GGGTGCTGAT TTGAATTCTA TGGTTAGAAA TTCCTTGTGT AATCCAATTC TTTTGTTTTC     3780

CTTTCTTTCT TGAGATGAAC CCCTCTTTTA GTTATTTCCA TGGATAACCT GTACTTGACT     3840

TATTCAGAAA TGATTTTCTA TTTTGCTGTA GAATCTGACA CTAAAGCTAA TAGCACTGAT     3900

GTTGCAGAGA GTTGAGACCA ACTTCCTGAG CTATGCTATA GATGATGCAC AGAAATATCC     3960

ATACCTTGCA TCAATGGGCA TTTATGTCTT CAAGAAAGAT GCACTTTTAG ACCTTCTCAA     4020

GTAATCACTT TCCTGTGACT TATTTCTATC CAACTCCTAG TTTACCTTCT AACAGTGTCA     4080

ATTCTTAGGT CAAAATATAC TCAATTACAT GACTTTGGAT CTGAAATCCT CCCAAGAGCT     4140

GTACTAGATC ATAGTGTGCA GGTAAGTCTG ATCTGTCTGG AGTATGTGTT CTGTAAACTG     4200

TAAATTCTTC ATGTCAAAAA GTTGTTTTTG TTTCCAGTTT CCACTACCAA TGCACGATTT     4260

ATGTATTTTC GCTTCCATGC ATCATACATA CTAACAATAC ATTTTACGTA TTGTGTTAGG     4320

CATGCATTTT TACGGGCTAT TGGGAGGATG TTGGAACAAT CAAATCATTC TTTGATGCAA     4380

ACTTGGCCCT CACTGAGCAG GTACTCTGTC ATGTATTCTG TACTGCATAT ATATTACCTG     4440

GAATTCAATG CATAGAATGT GTTAGACCAT CTTAGTTCCA TCCTGTTTTC TTCAATTAGC     4500

TTATCATTTA ATAGTTGTTG GCTAGAATTT AAACACAAAT TTACCTAATA TGTTTCTCTC     4560

TTCAGCCTTC CAAGTTTGAT TTTTACGATC CAAAAACACC TTTCTTCACT GCACCCCGAT     4620

GCTTGCCTCC GACGCAATTG GACAAGTGCA AGGTATATGT CTTACTGAGC ACAATTGTTA     4680

CCTGAGCAAG ATTTTGTGTA CTTGACTTGT TCTCCTCCAC AGATGAAATA TGCATTTATC     4740

TCAGATGGTT GCTTACTGAG AGAATGCAAC ATCGAGCATT CTGTGATTGG AGTCTGCTCA     4800

CGTGTCAGCT CTGGATGTGA ACTCAAGGTA CATACTCTGC CAATGTATCT ACTCTTGAGT     4860

ATACCATTTC AACACCAAGC ATCACCAAAT CACACAGAAC AATAGCAACA AGCCTTTTA     4920

GTTCAAGCA ATTTAGGGTA GCCTAGAGTT GAAATCTAAC AAAACAAAAG TCAAAGCTCT     4980

ATCACGTGGA TAGTTGTTTT CCATGCACTC TTATTTAAGC TAATTTTTTG GGTATACTAC     5040

ATCCATTTAA TTATTGTTTT ATTGCTTCTT CCCTTTGCCT TTCCCCCATT ACTATCGCGT     5100

CTTAAGATCA TACTACGCAC TAGTGTCTTT AGAGGTCTCT GGTGGACATG TTCAAACCAT     5160

CTCAATCGGT GTTGGACAAG TTTTTCTTGA ATTTGTGCTA CACCTAACCT ATCACGTATG     5220

TCATCGTTTC AAACTCGATC CTTCCTGTAT CATCATAAAT CCAATGCAAC ATACGCATTT     5280

ATGCAACATT TATCTGTTGA ACATGTCATC TTTTTGTAGG TTAACATTAT GCACCATACA     5340

ATGTAGCATG TCTAATCATC ATCCTATAAA ATTTACATTT TAGCTTATGT GGTATCCTCT     5400

TGCCACTTAG AACACCATAT GCTTGATGCC ATTTCATCCA CCCTGCTTTG ATTCTATGGC     5460

TAACATCTTC ATTAATATCC TCGCCTCTCT GTATCATTGG TCCTAAATAT GGAAATACAT     5520

TCTTTCTGGG CACTACTTGA CCTTCCAAAC TAACGTCTCC TTTGCTCCTT TCTTGTGTGT     5580

AGTAGTACCG AAGTCACATC TCATATATTC GGTTTTAGTT CTACTAAGTC CCGGGTTCGA     5640

TCCCCCTCAG GGGTGAATTT CGGGCTTGGT AAAAAAAATC CCCTCGCTGT GTCCCGCCCG     5700

CTCTCGGGGA TCGATATCCT GCGCGCCACC CTCCGGCTGG GCATTGCAGA GTGAGCAGTT     5760

GATCGGCTCG TTAGTGATGG GGAGCGGGGT TCAAGGGTTT TCTCGGCCGG GACCATGTTT     5820

CGGTCTCTTA ATATAATGCC GGGAGGGCAG TCTTTCCCTC CCCGGTCGAG TTTTAGTTCT     5880

ACCGAGTCTA AAACCTTTGG ACTCTAGAGT CCCCTGTCAC AACTCACAAC TCTAGTTTTC     5940

TATTTACTTC TACCTAGCGT TTATTAATGA TCACTATATC GTCTGTAAAA AGCATACACC     6000

AATGTAATCC CCTTGTATGT CCCTTGTAAT ATTATCCATC ACAAGAAAAA AAGGTAAGGC     6060
```

```
TCAAAGTTGA CTTTTGATAT AGTCCTATTC TAATCGAGAA GTCATCTGTA TCTTCGTCTC    6120

TTGTTCGAAC ACTAGTCACA AAATTTTTTG TACATGTTCT TAATGAGTCC AACGTAATAT    6180

TCCTTGATAT TTTGTCATAA GCCCTCATCA AGTCAATGAA AATCACGTGT AGGTCCTTCA    6240

TTTGTTCCTT ATACTGCTCC ATCACTTGTC TCATTAAGAA AATCTCTCTC ATAGTTAACC    6300

TTTTGGCATG AAACAAAATC ACACAGAAGT TGTTTCCTTT TTTTAAGATC CCACACAAAA    6360

GAGGTTTGAT CTAAGGAATC TGGATCCCTG ACAGGTTTAT CAAAATCCTT TGTGTTTTTC    6420

TTAAAACTGA ATATTCCTCC AGCTTCTAGT ATTGATGTAA TATTCAATCT GTTTAGCAAG    6480

TGAACACCTT GGTTCTTGTT GTTACTGTAC CCCCCCCCCC CCCCCCCCCC CGAGGCCCAG    6540

ATTACCACGA CATGAATACA AGAATATTGA ACCCAGATCT AGAGTTTGTT TGTACTGTTG    6600

AAAATCGGTG ACAATTCATT TTGTTATTGC GCTTTCTGAT AACGACAGGA CTCCGTGATG    6660

ATGGGAGCGG ACACCTATGA AACTGAAGAA GAAGCTTCAA AGCTACTGTT AGCTGGGAAG    6720

GTCCCAGTTG GAATAGGAAG GAACACAAAG ATAAGGTGAG TATGGATGTG GAACCACCGG    6780

TTAGTTCCCA AAAATATCAC TCACTGATAC CTGATGGTAT CCTCTGATTA TTTTCAGGAA    6840

CTGTATCATT GACATGAATG CTAGGATTGG GAAGAACGTG GTGATCACAA ACAGTAAGGT    6900

GAGCGAGCGC ACCTACATGG GTGCAGAATC TTGTGTGCTC ATCTATCCTA ATTCGGTAAT    6960

TCCTATCCAG CGCTAGTCTT GTGACCATGG GGCATGGGTT CGACTCTGTG ACAGGGCATC    7020

CAAGAGGCTA ATCACCCGGA AGAAGGGTAC TACATAAGGT CTGGAATCGT GGTGATCTTG    7080

AAGAATGCAA CCATCAACGA TGGGTCTGTC ATATAGATCG GCTGCGTGTG CGTCTACAAA    7140

ACAAGAACCT ACAATGGTAT TGCATCGATG GATCGTGTAA CCTTGGTATG GTAAGAGCCG    7200

CTTGACAGAA AGTCGAGCGT TCGGGCAAGA TGCGTAGTCT GGCATGCTGT TCCTTGACCA    7260

TTTGTGCTGC TAGTATGTAC TGTTATAAGC TGCCCTAGAA GTTGCAGCAA ACCTTTTTAT    7320

GAACCTTTGT ATTTCCATTA CCTGCTTTGG ATCAACTATA TCTGTCATCC TATATATTAC    7380

TAAATTTTTA CGTGTTTTTC TAATTCGGTG CTGCTTTTGG GATCTGGCTT CGATGACCGC    7440

TCGACCCTGG GCCATTGGTT CAGCTCTGTT CCTTAGAGCA ACTCCAAGGA GTCCTAAATT    7500

TTGTATTAGA TACGAAGGAC TTCAGCCGTG TATGTCGTCC TCACCAAACG CTCTTTTTGC    7560

ATAGTGCAGG GGTTGTAGAC TTGTAGCCCT TGTTTAAAGA GGAATTTGAA TATCAAATTA    7620

TAAGTATTAA ATATATATTT AATTAGGTTA ACAAATTTGG CTCGTTTTTA GTCTTTATTT    7680

ATGTAATTAG TTTTAAAAAT AGACCTATAT TTCAATACGA AATATCATTA ACATCGATA    7739
```